United States Patent

Tokoyoda et al.

Patent Number: 6,087,499
Date of Patent: Jul. 11, 2000

[54] PROCESS FOR PRODUCING 5-PERFLUOROALKYLURACIL DERIVATIVES

[75] Inventors: Kazuhiko Tokoyoda, Yamaguchi; Koji Kato, Chiba; Masami Takemitsu, Yamaguchi; Hiroaki Mizumoto, Yamaguchi; Shoji Arai, Yamaguchi, all of Japan

[73] Assignee: F-Tech Incorporated, Yamagushi, Japan

[21] Appl. No.: 09/129,344

[22] Filed: Aug. 5, 1998

[30] Foreign Application Priority Data

Aug. 7, 1997 [JP] Japan .................................. 9-212833
Nov. 26, 1997 [JP] Japan .................................. 9-324444

[51] Int. Cl.⁷ .............................................. C07D 239/02
[52] U.S. Cl. ........................................................ 544/303
[58] Field of Search ................................................ 544/303

[56] References Cited

U.S. PATENT DOCUMENTS 3,502,675  3/1970  Duschinsky et al. .................... 544/303

FOREIGN PATENT DOCUMENTS 0103436   3/1984   European Pat. Off. .
0635517   1/1995   European Pat. Off. .
58-174371 10/1983  Japan .
60-019771  1/1985  Japan .
08269020  10/1996  Japan .

OTHER PUBLICATIONS

Fuchikami et al., "An Effective and Convenient Route to 5–Trifluoromethyl–5–6–dihydrouracils and Their Thio Derivatives," *Synthesis*, (9), 766–768 (Sep. 1984).
Tandon et al., "Detection of New Metabolites of Trifluridine (F₃TdR) Using ¹⁹F NMR Spectroscopy," *Biochemical Pharmacology*, 44(11), 2223–2228 (Dec. 1, 1992).
Heidelberger et al., "Syntheses of 5–Trifluoromethyluracil and 5–Trifluoromethyl–2'–deoxyuridine," *J. Medicinal Chemistry*, 7(1), 1–5 (Jan. 8, 1964).

*Primary Examiner*—Gary Geist
*Assistant Examiner*—L. Eric Crane
*Attorney, Agent, or Firm*—McAulay Nissen Goldberg & Kiel, LLP

[57] ABSTRACT

A novel process is provided for producing a 5-perfluoroalkyl-5,6-dihydrouracil represented by General Formula (1):

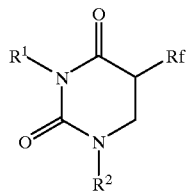

(where $R^1$ and $R^2$ are independently hydrogen, methyl, or ethyl, and Rf is a perfluoroalkyl of 1 to 10 carbons). The process comprises reacting α-perfluoroalkylacrylic acid represented by General Formula (2):

$$CH_2=C(Rf)-COOH \qquad (2)$$

with a urea derivative represented by General Formula (3):

$$R^1NHCONHR^2 \qquad (3)$$

in the presence of acetic anhydride with formed acetic acid being removed out of the reaction system during the reaction. The α-perfluoroalkylacrylic acid may be added successively. A process for producing a 5-perfluoroalkyl-5-bromo-6-hydrouracil by General Formula (4) is also provided:

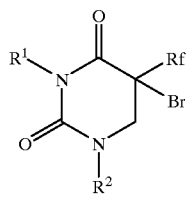

(where $R^1$, $R^2$, and Rf are as defined above)
wherein the reaction of a 5-perfluoroalkyl-5,6-dihydrouracil produced by the above process with bromine is conducted in water as the solvent. The process of the present invention can be industrially conducted safely and simply at a high yield.

14 Claims, No Drawings

PROCESS FOR PRODUCING 5-PERFLUOROALKYLURACIL DERIVATIVES

BACKGROUND OF THE INVENTION

1. Field of the Invention

The present invention relates to a process for producing a 5-perfluoroalkyluracil (hereinafter referred to as RfU) which is useful as a medicine intermediate. More specifically, the present invention relates to an improved process for producing a 5-perfluoroalkyluracil comprising a first production step of reacting an α-perfluoroalkylacrylic acid (hereinafter referred to as RfAA) with a urea derivative to obtain a 5-perfluoroalkyl-5,6-dihydrouracil (hereinafter referred to as RfDHU), and a second production step of reacting the RfDHU with bromine to produce a 5-perfluoroalkyl-5-bromo-6-hydrouracil (hereinafter referred to as RfBrU). The RfBrU is thermally decomposable into RfU readily and quantitatively. RfU is the main source material for 5-perfluoroalkyluridines and derivative thereof which are important as medicines such as anticancer medicines, antiviral medicines, and antiherpes medicines.

2. Description of the Related Art

A process for producing a RfDHU is known which employs a perfluoroalkyl methyl ketone (C. Heiderberger, D. G. Parrsons and D. C. Remy: J.Med.Chem. 7, 1 (1964)). This process, however, comprises a larger number of production steps, and produces the product at an overall yield of as low as 7 to 16%.

JP-A-58-174371 discloses a process for producing 5-trifluoromethyl-5,6-dihydrouracil (herein after referred to as TFMDHU) starting from 2-halo-3,3,3-trifluoropropene. This process produces TFMDHU at a low yield, being not suitable for industrial production.

JP-B-61-48830 discloses a process for producing RfDHUs starting from RfAA and a urea derivative. This process requires an expensive condensing agent like dicyclohexylcarbodiimide, and complicated separating operation after the reaction, being not suitable for industrial production.

JP-A-60-19771 and JP-A-8-269020 discloses a process for producing RfDHUs by reacting RfAA with a urea derivative in the presence of acetic anhydride or a like carboxylic acid anhydride at a relatively high yield of from 65 to 70%. The inventors of the present invention replicated carefully the disclose processes to obtain a solid product, so-called TFMDHU, at an yield of about 75%. However, the obtained solid product of TFMDHU contained a large amount of acetyl urea as a byproduct as the result of precise analysis by the inventors of the present invention, and the actual TFMDHU yield was found to be as low as 42.7%.

JP-A-8-269020 discloses a process for purifying the produced TFMDHU in which the TFMDHU yield is improved to 70% at the molar ratio of RfAA to the urea derivative of from 1.0 to 1.5.

JP-A-61-254538 discloses a process of reacting 2-hydroxymethyl-3,3,3-trifluoropropionic acid with urea in the presence of acetic anhydride. This process involves longer reaction step, being not necessarily advantageous in view of the production cost and the overall yield.

On the other hand, as the second step, RfBrU can be produced by reaction of RfDHU and bromine. For example, in a known method, TFMDHU is reacted with bromine in acetic acid as the solvent (C. Heiderberger, et al.: J.Med-.Chem. 7, 1 (1964)). This method requires a larger excess amount of bromine, two or more moles per mole of TFMDHU, and produces an irritating bromoacetic acids as a byproduct during the reaction process by bromination of the solvent acetic acid.

JP-A-60-94971 discloses a process of brominating a RfDHU with cupric bromide in a solvent containing a dialkyl carboxylic acid amide. This process gives a large amount of waste liquid after the reaction, and involves problems in operation and after-treatment.

JP-A-7-33750 discloses a process for producing 5-trifluoromethyluracil (hereinafter referred to as TFMU) by reacting RfDHU with halogen in an alkylsulfoxide in the presence of an acid catalyst in an alkylsulfoxide to produce 5-trifluoromethyl-5-halogeno-6-hydrouracil as the intermediate, and dehydrohalogenating the intermediate without isolating it. This process requires expensive iodine as the source material, and gives a large amount of waste liquid composed of the organic solvent containing the inorganic acid.

In either of the aforementioned JP-A-60-94971 or JP-A-7-33750, a purification process for the formed RfBrU is required: for example, recrystallization from ethanol or water, or extraction. Even with such purification step, a product of high purity cannot readily be produced.

The inventors of the present invention studied the process for producing an RfDHU as the first step by reacting RfAA with urea derivative in the presence of acetic anhydride. Consequently, the reaction was found to generates a great quantity of the reaction heat, when the source materials are charged together at one time, to render the reaction temperature uncontrollable industrially, resulting in low yield, disadvantageously as disclosed in JP-A-60-19771 and JP-A-8-269020. The heat of formation of the reaction product is estimated to be about 30 kcal/mol from the data in MOPAC (Ver.6) PM3, and Kagaku Binran [Kisohen II] (Chemical Handbook [Basic Data Collection II]).

Further, the inventors of the present invention studied the second step of the process for producing an RfBrU of high purity at a low cost.

SUMMARY OF THE INVENTION

An object of the present invention is to provide a safe industrial process for producing an RfDHU as the first step which gives the objective product at a high yield with controlled heat generation.

Another object of the present invention is to provide an improved process for producing an RfBrU as the second step which gives the objective product of high purity safely and simply at a low cost without forming a waste liquid or a residue which is not readily disposable.

The process of the present invention for producing an RfDHU represented by General Formula (1):

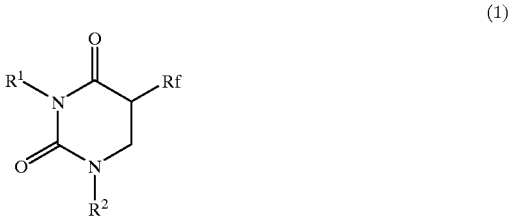

(1)

(where Rf is a perfluoroalkyl of 1 to 10 carbons) comprises reacting RfAA represented by General Formula (2):

$CH_2=C(Rf)—COOH$ (2)

with a urea derivative represented by General Formula (3):

(where $R^1$ and $R^2$ are independently hydrogen, methyl, or ethyl) in the presence of acetic anhydride with formed acetic acid being removed out of the reaction system. The RfAA may be added successively, and the formed acetic acid may be removed out of the reaction system during the reaction. The molar ratio of the total amount of the urea derivative to RfAA ranges preferably from 1.5 to 4.0.

The process of the present invention for producing an RfBrU represented by General Formula (4):

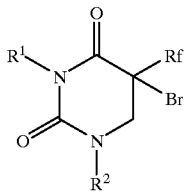

(where $R^1$ and $R^2$ are as defined above) comprises reacting the RfDHU produced above and represented by General Formula (3) with bromine in a water as the solvent. Rf may be trifluoromethyl, and $R^1$ and $R^2$ may be hydrogen respectively in General Formulas (1) and (4).

DETAILED DESCRIPTION OF THE PREFERRED EMBODIMENT

The source materials used in the present invention are RfAA, an urea derivative, acetic anhydride, bromine, and water.

RfAA in the present invention is an α-substituted acrylic acid having a perfluoroalkyl group on an a carbon as shown by General Formula (2). The perfluoroalkyl group is a perfluorinated alkyl group of 1 to 10 carbons. The RfAA specifically includes α-trifluoromethylacrylic acid (hereinafter referred to as TFMAA), and α-pentafluoroethylacrylic acid. The RfAA has preferably a purity of not lower than 95%, but is not limited thereto. The RfAAs are usually solid, and may be handled in a state of powder, but is preferably handled in a liquid state of a solution in acetic anhydride.

The urea derivative in the present invention is a compound represented by General Formula (3), specifically including urea, methylurea, ethylurea, dimethylurea, and diethylurea. Of these, urea and methylurea are preferred. The purity thereof is preferably not lower than 95%, but is not limited thereto. The urea derivative is usually solid, and may be added to the reaction system in a state of powder, but is preferably added in a liquid state of a solution or slurry in acetic anhydride.

The RfDHU in the present invention is a compound represented by General Formula (1), specifically including TFMDHU (Formula 1-1), 1-methyl-5-trifluoromethyl-5,6-dihydrouracil (Formula 1-2), and 3-methyl-5-trifluoromethyl- 5,6-dihydrouracil (Formula 1-3):

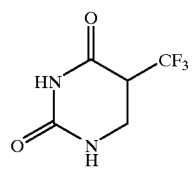

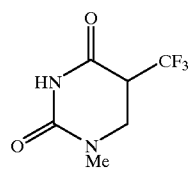

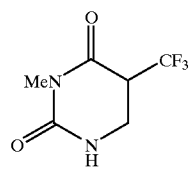

The RFDHU contains frequently acetylurea. Although the contained acetylurea causes no difficulty, the purity of the RfDHU is not lower than 50% by weight, since the RfDHU increases bromine consumption in conducting the reaction. The contents of impurities other than acetylurea are preferably as low as possible. If necessary, the RfDHU is purified by recrystallization from ethanol, or a like purification method.

The acetic anhydride and the bromine as the source materials may be commercial products. The water as the solvent in the present invention is preferably deionized water, but is not limited thereto.

The RfBrU, the intended product of the present invention, is a compound represented by General Formula (4) shown above, specifically including 5-trifluoromethyl-5-bromo-6-hydrouracil (Formula 4-1, hereinafter referred to as TFMBrU), 1-methyl-5-trifluoromethyl-5-bromo-6-hydrouracil (Formula 4-2), and 3-methyl-5-trifluoromethyl-5-bromo-6-hydrouracil (Formula 4-3):

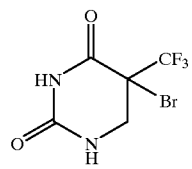

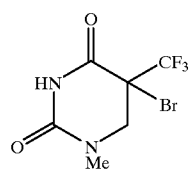

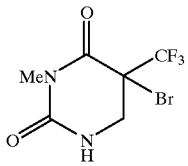
(4-3)

The reaction is conducted with these source materials.

The reaction of the first step is conducted, for example, in a reactor equipped with a stirrer, a liquid dropping device, a thermometer, and cooling device. The process of the present invention is characterized in that the reaction is conducted with removal of formed acetic acid out of the system during the reaction, and that the source materials are successively added to the reaction system in a specific method to control the heat of the product formation. Generally, the reaction can be conducted by any of the reaction types below.

(1) A solution of RfAA in acetic anhydride and a solution of a urea derivative in acetic anhydride are added at one time into an acetic anhydride solvent.
(2) A solution of RfAA in acetic anhydride and a solution of a urea derivative in acetic anhydride are concurrently added dropwise into an acetic anhydride solvent.
(3) A solution of RfAA in acetic anhydride is added successively into a solution of a urea derivative in acetic anhydride.
(4) A solution of a urea derivative in acetic anhydride is added successively into a solution of RfAA in acetic anhydride.

The reaction of Type (1) can be conducted in a small scale, but is not suitable for industrial production since the temperature rise of the reaction system by the reaction heat is excessively large. The reaction of Type (4) is not preferred since the product yield is lower owing to occurrence of polymerization of PfAA and polyaddition of PfAA with urea. The specific method of successive reaction of the source materials in the present invention means the methods of Type (2) and Type (3) which enable the reaction to proceed at a high yield with control of the heat of the product formation reaction. Of the two types of the method, Type (3) is preferred in view of the solubilities and the amounts of the source materials, and ease of operation.

The reaction by successive addition of the present invention is usually conducted in one to three hours by controlling the reaction heat generation and the cooling rate thereof, and the reaction mixture is allowed to age preferably for 30 minutes to one hour. The rate of stirring during the reaction is not limited, and is selected depending on the shape of the reactor and the shape of the stirring blade, usually ranging from 200 to 1600 rpm.

The atmosphere for the reaction in the present invention is not limited. However, an inert gas atmosphere such as nitrogen, and argon is preferred.

In the reaction, acetic acid is formed with the progress of the reaction in the reaction system: 2 moles of acetic acid is formed for the formation of one mole of RfDHU (1). The formed acetic acid lowers the reactivity of the system of the instant reaction, causing formation of an addition product with the urea derivative or competitive reaction with RfAA to lower the intended product yield.

According to the present invention, the reaction is carried out efficiently by removing the formed acetic acid from the reaction system during the reaction, for example, under a reduced pressure ranging from 50 to 500 mmHg. By this operation, the excess of the urea derivative is saved, and the intended RfDHU is obtained at a high yield. The molar ratio of the urea derivative ranges usually from 1.1 to 2.0, preferably from 1.1 to 1.5 relative to RfAA depending on the removal rate of the acetic acid.

In the case where the formed acetic acid is not removed out of the reaction system in the present invention, the urea derivative should be added in a large excess for obtaining the intended product at a high yield. In this case, the amount is in the range from 1.5 to 4.0 moles, preferably from 1.5 to 3.0 moles per mole of RfAA. With the amount of less than 1.5 moles, the product yield decreases remarkably, whereas with the amount of more than 4.0 moles, the excessive urea derivative makes difficult the stirring or the product purification to render the process uneconomical industrially.

The process of the present invention is practiced at a temperature ranging from 70 to 110° C., preferably from 80 to 100° C. At the reaction temperature lower than 70° C., the reaction velocity is low, resulting in a low product yield, whereas at the reaction temperature higher than 110° C., the selectivity of the RfDHU is lower and decomposition may occur disadvantageously.

The amount of the acetic anhydride is in the range of three to ten times, preferably three to six times that of RfAA by weight. With the amount of the acetic anhydride larger than six times that of RfAA, a larger reactor is required uneconomically.

After the reaction, the reaction mixture is vacuum-distilled to remove acetic anhydride and acetic acid to obtain a concentrated RfDHU solution. The separated acetic anhydride may be reused after purification as necessary. The concentrated RfDHU solution is heated with a large amount of ethanol added thereto, and cooled to room temperature, whereby the intended RfDHU crystallizes out. The ethanol is used usually in an amount to obtain a solution of a RfDHU concentration ranging from 15% to 35% by weight. At the concentration of lower than 15% by weight, the yield of the crystal is lower owing to dissolution in the mother liquor, whereas at the concentration of higher than 35% by weight, the quality of the obtained crystals is lower owing to incomplete dissolution of the crystal. The crystallized RfDHU is collected by filtration, and is dried to obtain the intended RfDHU (primary crystals). The mother liquor is concentrated, for example, by a rotary evaporator to crystallize out further the RfDHU (secondary crystals). Thus RfDHU can be obtained in a high yield by combining the primary crystals and the secondary crystals.

In the second step reaction, the RfDHU obtained in the above process is reacted with bromine. The reaction is conducted, for example, by preparing a homogeneous solution of RfDHU in water by mixing water and RfDHU with heating and stirring in a reactor equipped with a stirrer, a thermometer, and a liquid-dropping device, and adding bromine successively.

The water is used, in the present invention, in an amount necessary for dissolving completely the RfDHU. Usually water is used in an amount of 10 to 60 times, preferably 14 to 20 times that of the RfDHU by weight. With the amount of water less than that RfDHU, the source material, is not completely dissolved, whereas with the amount of water larger than that, the yield is lower.

The bromination reaction temperature is in the range from 60 to 110° C., preferably from 80 to 100° C. in the present invention. At the temperature lower than that, the reaction velocity is lower and is not efficient, whereas at a temperature higher than 110° C., the source material may be decomposed or the product yield is lower undesirably.

The bromine as the source material is added successively with stirring into the reaction system in the process of the present invention. The bromine is added preferably at such a rate that the red brown color of the bromine does not become strong during the reaction. The amount of the bromine is preferably in the range from 1.01 to 3 moles per mole of the RfDHU. When the purity of RfDHU is low, the bromine should be added in a suitably increased amount. The bromine addition takes time of 3 to 8 hours. The end point of the bromination can be readily recognized by stop of disappearance of bromine color during the reaction.

After the reaction, the reaction mixture is allowed to age for a time of 8 to 12 hours for complete reaction of the RfDHU. With the shorter aging time, an unbrominated source material may remain, whereas with a longer aging time, the reaction efficiency is lower undesirably. The rate of stirring is usually in the range from 400 to 1500 rpm, but is not limited thereto. The reaction pressure is not limited: atmospheric pressure is acceptable, but may be pressurized if necessary. The reaction atmosphere may be air, but preferably an inert atmosphere such as nitrogen and argon.

The end product, RfBrU represented by General Formula (4), partly crystallizes out during the reaction. The liquid reaction mixture is cooled to room temperature to increase the recovery of the product. The cooling is conducted for 3 to 5 hours, more preferably overnight for crystal growth to facilitate the separation by filtration. Before the filtration, the remaining excess bromine may be removed by nitrogen blowing, or addition of hydrazine. Otherwise, the excess bromine and hydrogen bromide may be removed by neutralization with an alkali.

The needle crystalline matter separated from water by filtration, centrifugation, or a like method is an RfBrU having a purity of not lower than 98% It can be purified by recrystallization from water if necessary. The RfBrU obtained thus can readily be converted to RfU by heating decomposition in N-methylpyrrolidone as the solvent.

The present invention is described below more specifically by reference to examples without limiting the invention thereto.

EXAMPLE 1

In 300-mL four-neck flask equipped with a stirrer, a dropping funnel, a thermometer, and a cooling device, were placed 72.0 g (0.71 mol) of acetic anhydride (commercial product, produced by The Nippon Synthetic Chemical Industry Co., Ltd.), and 17.4 g (0.29 mol) of urea (commercial product, produced by Mitsui Toatsu Chemicals, Inc.). The mixture was heated to 90° C. with stirring at 800 rpm in a nitrogen atmosphere. The urea-containing mixture was in a slurry state. Thereto a solution of 20.0 g (0.14 mol) of TFMAA (purity: 95.3%, produced by F-Tech Inc.) in 28.0 g (0.27 mol) of acetic anhydride was added dropwise over two hours by keeping the reaction temperature in the range from 90 to 95° C. Immediately after the start of the reaction, the reaction system was evacuated and the internal pressure was kept at 150 mmHg. Thereby, the acetic acid formed in the system was recovered in an amount of 14.0 g (83.3% of calculated amount). After the completion of the addition of TFMMA, the reaction mixture was allowed to age for 45 minutes. After the aging, the reaction mixture was evacuated by a vacuum pump, and the acetic anhydride and the acetic acid was separated by vacuum distillation to obtain a concentrated reaction mother liquor. Thereto, 125 mL of ethanol was added. The mixture was heated, and then cooled to room temperature to crystallize out TFMDHU. The crystalline matter was collected by filtration from the mother liquor. The obtained crystalline FMDHU was dried to obtain 20.5 g of primary crystals (estimated by high-speed liquid chromatography according to internal standard method). Further, the mother liquor was concentrated under a reduced pressure to obtain secondary TFMDHU crystals. Thereby, 0.6 g of the secondary crystalline TMFDHU was obtained. The total yield of the combined primary and secondary crystals was 82.8% based on TFMAA. The acetylurea was formed as the by-product in an amount of 3.6 g.

| TFMDHU: | |
|---|---|
| m.p.: | 203–205° C. (decomposed) (Literature value: 203–205° C. (decomposed)) |
| IR (KBr): | 3500–2750 cm$^{-1}$ ($v_{N-H}$) 1725, 1750 cm$^{-1}$ ($v_{C=O}$) |
| $^1$H NMR (d$_6$-DMSO, TMS): | σ 3.4–4.0 (m, 3H), 7.8 (bs, 1H) 10.5 (bs, 1H) |
| $^{19}$F NMR (d$_6$-DMSO, CFCl$_3$): | σ −65.6 (d) |

EXAMPLE 2

In the same reactor as that employed in Example 1, were placed 48.0 g (0.47 mol) of acetic anhydride, and 17.1 g (0.29 mol) of urea. Thereto, a solution of 20.0 g (0.14 mol) of TFMAA in 28.0 g (0.27 mol) of acetic anhydride was added dropwise over two hours under the same reaction conditions as in Example 1 without application of vacuum. After completion of the addition, the reaction mixture was allowed to age for 45 minutes. After the aging, the primary and secondary crystalline TFMDHU were collected in the same manner as in Example 1. The total yield of the crystalline TFMDHU was 19.4 g (76.1% based on TFMAA). The acetylurea was formed in an amount of 9.6 g.

EXAMPLE 3

In the same reactor as that employed in Example 1, were placed 72.0 g (0.71 mol) of acetic anhydride, and 12.6 g (0.21 mol) of urea. Thereto, a solution of 20.0 g (0.14 mol) of TFMAA in 28.0 g (0.27 mol) of acetic anhydride was added dropwise over two hours under the same reaction conditions as in Example 1. Immediately after the start of the reaction, the system was evacuated and kept at 150 mmHg to recover 11.9 g (70.8% of calculated amount) of acetic acid formed in the reaction system. After completion of the addition, the reaction mixture was allowed to age for 45 minutes. After the aging, the primary crystalline TFMDHU and the secondary crystalline TFMDHU were collected in the same manner as in Example 1. The total yield of the crystalline TFMDHU was 17.5 g (68.6% based on TFMAA). The acetylurea was formed as the by-product in an amount of 6.3

COMPARATIVE EXAMPLE 1

In the same reactor as that employed in Example 1, were placed 48.0 g (0.47 mol) of acetic anhydride, and 9.2 g (0.15 mol) of urea. Thereto, a solution of 20.0 g (0.14 mol) of TFMAA in 28.0 g (0.27 mol) of acetic anhydride was added dropwise over two hours under the same reaction conditions as in Example 1. After completion of the addition, the reaction mixture was allowed to age for 45 minutes. After the aging, the primary TFMDHU and the secondary crystalline TFMDHU were collected in the same manner as in Example 1. The total yield of the crystalline TFMDHU was 6.4 g (25.1% based on TFMAA). The acetylurea was formed in an amount of 11.2 g.

COMPARATIVE EXAMPLE 2

In the same reactor as that employed in Example 1, were placed 48.0 g (0.47 mol) of acetic anhydride, and 20.0 g (0.14 mol) of TFMAA. Thereto, a solution of 9.2 g (0.15 mol) of urea in 28.0 g (0.27 mol) of acetic anhydride was added dropwise over two hours under the same reaction conditions as in Example 1. After completion of the addition, the reaction mixture was allowed to age for 45 minutes. After the aging, the primary TFMDHU and the secondary crystalline TFMDHU were collected in the same manner as in Example 1. The total yield of the crystalline TFMDHU was 4.5 g (17.6% based on TFMAA). The acetylurea was formed in an amount of 5.4 g.

EXAMPLE 4

In the same reactor as that employed in Example 1, was placed 40.0 g (0.39 mol) of acetic anhydride. Thereto, a solution of 20.0 g (0.14 mol) of TFMAA in 28.0 g (0.27 mol) of acetic anhydride, and a solution of 25.2 g (0.42 mol) of urea in 32.0 g (0.31 mol) were added dropwise concurrently over two hours under the same reaction conditions as in Example 1. Immediately after the start of the reaction, the system was evacuated and kept at 150 mmHg to recover 10.5 g (62.5% of calculated amount) of acetic acid formed in the reaction system. After completion of the addition, the reaction mixture was allowed to age for 45 minutes. After the aging, the primary and secondary crystalline TFMDHU were collected in the same manner as in Example 1. The total yield of the crystalline TFMDHU was 16.1 g (63.1% based on TFMAA). The acetylurea was formed in an amount of 8.1 g.

EXAMPLE 5

In the same reactor as that employed in Example 1, was placed 40.0 g (0.39 mol) of acetic anhydride. Thereto, a solution of 20.0 g (0.14 mol) of TFMAA in 28.0 g (0.27 mol) of acetic anhydride, and a solution of 24.6 g (0.41 mol) of urea in 32.0 g (0.31 mol) of acetic anhydride were added dropwise concurrently over two hours under the same reaction conditions as in Example 1. After completion of the addition, the reaction mixture was allowed to age for 45 minutes. After the aging, the primary and secondary crystalline TFMDHU were collected in the same manner as in Example 1. The total yield of the crystalline TFMDHU was 13.8 g (54.1% based on TFMAA). The acetylurea was formed in an amount of 9.8 g.

COMPARATIVE EXAMPLE 3

In the same reactor as that employed in Example 1, was placed 40.0 g (0.39 mol) of acetic anhydride. Thereto, a solution of 20.0 g (0.14 mol) of TFMAA in 28.0 g (0.27 mol) of acetic anhydride, and a solution of 9.0 g (0.15 mol) of urea in 32.0 g (0.31 mol) were added dropwise concurrently over two hours under the same reaction conditions as in Example 1. After completion of the addition, the reaction mixture was allowed to age for 45 minutes. After the aging, the primary crystalline TFMDHU and the secondary crystalline TFMDHU were collected in the same manner as in Example 1. The total yield of the crystalline TFMDHU was 6.1 g (23.9% based on TFMAA). The acetylurea was formed in an amount of 10.5 g.

EXAMPLE 6

In the same reactor as that employed in Example 1, were placed 62.2 g (0.61 mol) of acetic anhydride, 9.0 g (0.15 mol) of urea, and 20.0 g (0.14 mol) of TFMAA. Heating was started from room temperature with stirring at 800 rpm under nitrogen atmosphere. The reaction temperature rose spontaneously up to 118° C. Immediately after start of the reaction, the system was evacuated and kept at 150 mmHg to recover 11.6 g (69.0% of calculated amount) of the formed acetic acid. After reaching the maximum temperature, the reaction mixture was allowed to age for 45 minutes. After the aging, the primary crystalline TFMDHU and secondary crystalline TFMDHU were collected in the same manner as in Example 1. The total yield of the crystalline TFMDHU was 12.3 g (48.2% based on TFMAA). The acetylurea was formed in an amount of 8.5 g.

COMPARATIVE EXAMPLE 4

In the same reactor as that employed in Example 1, were placed 62.2 g (0.61 mol) of acetic anhydride, 9.0 g (0.15 mol) of urea, and 20.0 g (0.14 mol) of TFMAA. Heating was started from room temperature with stirring at 800 rpm under nitrogen atmosphere. The reaction temperature rose spontaneously up to 120° C. The reaction was conducted for one hour. After reaching the maximum temperature, the reaction mixture was allowed to age for 45 minutes. After the aging, the primary crystalline TFMDHU and secondary crystalline TFMDHU were collected in the same manner as in Example 1. The total yield of the crystalline TFMDHU was 10.9 g (42.7% based on TFMAA). The acetylurea was formed in an amount of 9.9 g.

EXAMPLE 7

To 146 mL of water, was added 10.0 g (54.9 mmol) of TFMDHU (98.3% pure, produced by F tech Co.) (weight ratio of 14.6:1). The mixture was heated to 90° C. to obtain a homogeneous solution. Thereto, 9.7 g (1.1 equivalents) of bromine (commercial product, produced by Tosoh Corp.) was added dropwise with stirring over 6 hours by keeping the temperature not lower than 85° C. After the addition of bromine, the reaction mixture was allowed to age at 90° C. with stirring for 11 hours. The reaction mixture was then cooled to 20° C. to deposit a crystalline matter. The deposited white needle crystalline TFMBrU was collected by filtration to obtain 12.6 g (88.0% based on TFMDHU) of TFMBrU of a purity of 99.2%

| TFMBrU: | |
|---|---|
| m.p.: | 224–228° C. (decomposed) (Literature value: 224–228° C. (decomposed)) |
| $^1$H NMR (d$_6$-DMSO, TMS): | σ 3.4–4.0 (m, 2H), 8.3 (d, 1H) 11.0 (bs, 1H) |
| $^{19}$F NMR (d$_6$-DMSO, CFCl$_3$): | σ −69.3 (d) |

EXAMPLE 8

TFMBrU was prepared in the same manner as in Example 7 except that the amount of the bromine was changed to 11.4 g (1.3 equivalents). Consequently, TFMBrU of 98.3% pure was obtained in a yield of 12.3 g (85.8% based on TFMDHU).

EXAMPLE 9

TFMBrU was prepared in the same manner as in Example 7 except that the amount of the water was changed to 175 mL (weight ratio of 17.5:1). Consequently, TFMBrU of 98.4% pure was obtained in a yield of 11.7 g (81.7% based on TFMDHU).

EXAMPLE 10

TFMBrU was prepared in the same manner as in Example 7 except that the amount of the water was changed to 521 mL (weight ratio of 52.1:1). Consequently, TFMBrU of 98.1% pure was obtained in a yield of 9.9 g (69.1% based on TFMDHU).

EXAMPLE 11

In 120 mL of water, was added 10 g of 73.5% TFMDHU (7.4 g, 40.6 mmol of pure TFMDHU) prepared in Example 3 containing acetylurea at a content of 26.5% as an impurity. The mixture was heated to 90° C. to dissolve the TFMDHU. Thereto, 9.7 g (1.5 equivalents) of bromine was added dropwise over 4 hours. After completion of the addition, the mixture was stirred with heating for 10 hours. Then the reaction mixture was cooled to room temperature to deposit crystalline matter. The crystalline matter was collected by filtration to obtain 9.0 g of TFMBrU (84.9% based on TFMDHU) of 98.2% pure.

EXAMPLE 12

In 160 mL of water, was added 10 g of 58.5% TFMDHU (5.9 g, 32.4 mmol of pure TFMDHU) prepared in Example 5 containing acetylurea at a content of 41.5% as an impurity. The mixture was heated to 90° C. to dissolve the TFMDHU. Thereto, 25.4 g (4.9 equivalents) of bromine was added dropwise with stirring over 4 hours. After completion of the addition, the mixture was stirred with heating for 10 hours. Then the reaction mixture was cooled to room temperature to deposit a crystalline matter. The crystalline matter was collected by filtration to obtain 5.6 g of TFMBrU (73.3% based on TFMDHU) of 99.0% pure.

COMPARATIVE EXAMPLE 5

In 60 mL of acetic acid, was dissolved 10 g (54.9 mmol) of TFMDHU. The mixture was heated to 90° C. Thereto, 17.6 g (2.0 equivalents) of bromine was added dropwise with stirring over 4 hours. After the completion of the addition, the mixture was stirred with heating for 10 hours. The acetic acid was distilled off, and ethanol was added thereto. The mixture was once heated, and then cooled to deposit a crystalline matter. During the reaction, an irritating by-product, which was estimated to be a bromoacetic acid derivative, was formed, so that great care was taken for removing the solvent and collecting the crystalline matter. The collected crystalline matter amounted to 9.9 g (yield 69.1%) of TFMBrU of 94.8% pure. This crystalline TFM-BrU contained TFMDHU, the source material, at a content of 5.2%. The purity of the TFMDHU could not be raised by repeated recrystallization from ethanol-water.

According to the first step of the present invention, an RfDHU can be produced safely at a high yield industrially by controlling the heat generation.

According to the second step of the present invention, a high-purity TFMBrU can be produced safely and simply at a high yield without forming a waste liquid or waste residue which cannot readily be discarded.

According to the present invention, the end product of the RfU derivative can be synthesized readily.

What is claimed is:

1. A process for producing a 5-perfluoroalkyl-5,6-dihydrouracil represented by formula (1):

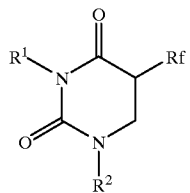

(1)

where $R^1$ and $R^2$ are independently hydrogen, methyl or ethyl, and Rf is a perfluoroalkyl of 1 to 10 carbons, the process comprising combining
an α-perfluoroalkylacrylic acid represented by formula (2):

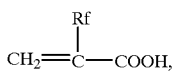

(2)

a urea derivative represented by formula (3):

(3)

and
acetic anhydride,
and reacting the combination, while removing acetic acid formed during the reaction.

2. The process of claim 1 having a mole ratio of the total of the urea derivative to the α-perfluoroalkylacrylic acid in the range from 1.1 to 2.0.

3. The process of claim 1 having a mole ratio of the total of the urea derivative to the α-perfluoroalkylacrylic acid in the range from 1.1 to 1.5.

4. A process for producing a 5-perfluoroalkyl-5,6-dihydrouracil represented by formula (1):

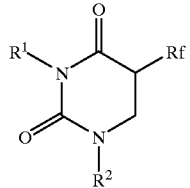

(1)

where $R^1$ and $R^2$ are independently hydrogen, methyl or ethyl, and Rf is a perfluoroalkyl of 1 to 10 carbons, the process comprising:
combining a urea derivative represented by formula (3):

(3)

and acetic anhydride;
adding over a period of time an α-perfluoroalkylacrylic acid represented by formula (2):

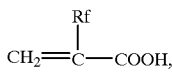

(2)

to cause reaction; and removing acetic acid formed during the reaction.

5. The process for producing a 5-perfluoroalkyl-5,6-dihydrouracil according to claim 4, wherein a mole ratio of the total of the urea derivative to the α-perfluoroalkylacrylic acid ranges from 1.1 to 2.0.

6. The process for producing a 5-perfluoroalkyl-5,6-dihydrouracil according to claim 4, wherein a mole ratio of the total of the urea derivative to the α-perfluoroalkylacrylic acid ranges from 1.1 to 1.5.

7. A process for producing a 5-perfluoroalkyl-5-bromo-6-hydrouracil represented by formula (4):

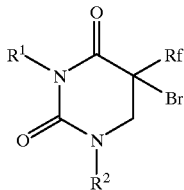

(4)

where $R^1$ and $R^2$ are independently hydrogen, methyl or ethyl, and Rf is a perfluoroalkyl of 1 to 10 carbons, the process comprising:

producing a 5-perfluoroalkyl-5,6-dihydrouracil by combining an α-perfluoroalkylacrylic acid represented by formula (2):

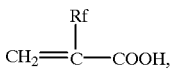

(2)

a urea derivative represented by formula (3):

 (3)

and acetic anhydride, and
reacting the combination while removing acetic acid formed during the reaction; and reacting the 5-perfluoroalkyl-5,6-dihydrouracil with bromine in water.

8. The process for producing a 5-perfluoroalkyl-5-bromo-6-hydrouracil according to claim 7, wherein Rf is trifluoromethyl, and $R^1$ and $R^2$ are respectively hydrogen in general formulas (3) and (4).

9. The process of claim 7 having a mole ratio of the total of the urea derivative to the α-perfluoroalkylacrylic acid in the range from 1.1 to 2.0.

10. The process of claim 7 having a mole ratio of the total of the urea derivative to the α-perfluoroalkylacrylic acid in the range from 1.1 to 1.5.

11. A process for producing a 5-perfluoroalkyl-5-bromo-6-hydrouracil represented by formula (4):

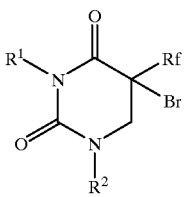

(4)

where $R^1$ and $R^2$ are independently hydrogen, methyl or ethyl, and Rf is a perfluoroalkyl of 1 to 10 carbons, the process comprising:

combining a urea derivative represented by formula (3):

 (3)

and acetic anhydride,
adding over a period of time an α-perfluoroalkylacrylic acid represented by formula (2):

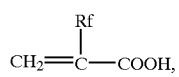

(2)

to cause reaction, and removing acetic acid formed during the reaction; and reacting the 5-perfluoroalkyl-5,6-dihydrouracil with bromine in water.

12. The process of claim 11 having a mole ratio of the total of the urea derivative to the α-perfluoroalkylacrylic acid in the range from 1.1 to 2.0.

13. The process of claim 11 having a mole ratio of the total of the urea derivative to the α-perfluoroalkylacrylic acid in the range from 1.1 to 1.5.

14. The process for producing a 5-perfluoroalkyl-5-bromo-6-hydrouracil according to claim 11, wherein Rf is trifluoromethyl, and $R^1$ and $R^2$ are hydrogen in formulas (3) and (4), respectively.

* * * * *